United States Patent [19]

Cook et al.

[11] Patent Number: 5,073,548
[45] Date of Patent: Dec. 17, 1991

[54] 11 β-SUBSTITUTED PROGESTERONE ANALOGS

[75] Inventors: C. Edgar Cook; Mansukh C. Wani, both of Durham; Yun W. Lee, Chapel Hill; Jerry R. Reel, Cary, all of N.C.; Douglas Rector, Mobile, Ala.

[73] Assignee: Research Triangle Institute, Research Triangle Park, N.C.

[21] Appl. No.: 504,129

[22] Filed: Apr. 3, 1990

Related U.S. Application Data

[62] Division of Ser. No. 210,503, Jun. 23, 1988, Pat. No. 4,954,490.

[51] Int. Cl.$^5$ .................. C07J 17/00; A61K 31/58
[52] U.S. Cl. .................. 514/169; 514/177; 514/179; 552/520; 552/603; 552/605; 552/608; 552/514
[58] Field of Search ............... 552/520, 603, 605, 608, 552/514; 514/177, 179, 169

[56] References Cited

U.S. PATENT DOCUMENTS

| 4,386,085 | 5/1983 | Teutsch et al. | 552/520 |
| 4,477,445 | 10/1984 | Philibert et al. | 514/177 |
| 4,540,686 | 9/1985 | Philibert et al. | 514/177 |

OTHER PUBLICATIONS

Neef et al., Chemical Abstracts vol. 104, 1986 Abstract 34230f.

Primary Examiner—Mukund J. Shah
Assistant Examiner—E. C. Ward
Attorney, Agent, or Firm—Oblon, Spivak, McClelland, Maier & Neustadt

[57] ABSTRACT

A 11β-aryl-19-norprogesterone steroid of the formula:

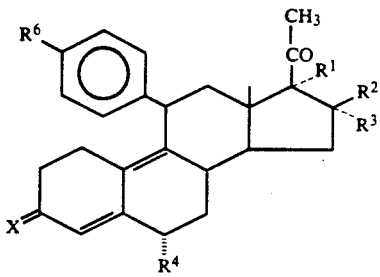

wherein (i) $R^1$ is H, $C_{1-4}$ alkyl, $C_{2-4}$ alkenyl, $C_{2-4}$ alkynyl, OH, OC(O)CH$_3$, or OC(O)R$^5$, wherein $R^5$ is $C_{2-8}$ alkyl, $C_{2-8}$ alkenyl, $C_{2-8}$ alkynyl or aryl, $R_2$ is H, $R^3$ is H, $C_{1-4}$ alkyl, $C_{2-4}$ alkenyl or $C_{2-4}$ alkynyl, $R^4$ is H, CH$_3$, F or Cl, $R^6$ is H, (CH$_3$)$_2$N, CH$_3$O, CH$_3$CO, CH$_3$S, CH$_3$SO, CH$_3$SO$_2$, and X is O or NOCH$_3$; or (ii) $R^1$ and $R^2$ taken together are a carbon-carbon bond and $R^3$, $R^4$, $R^6$ and X are as defined above; or (iii) $R^1$ and $R^3$ taken together are —CH$_2$— or —N=N—CH$_2$—, $R^2$ is H and $R^4$, $R^6$ and X are as defined above; or (iv) $R^2$ and $R^3$ taken together are =CH$_2$ and $R^1$, $R^4$, $R^6$ and X are as defined above.

16 Claims, 2 Drawing Sheets

IV

Structure of Compounds of This Invention
($R^1 - R^6$ and X are Defined in the Text)

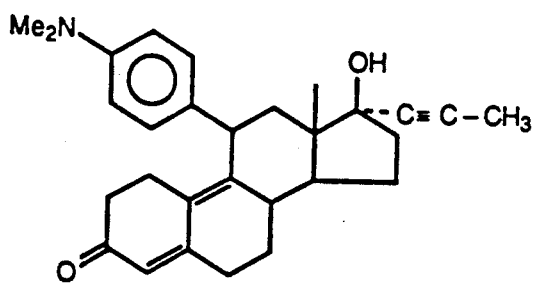
I
[RU – 38.486 (ZK 95.890)]
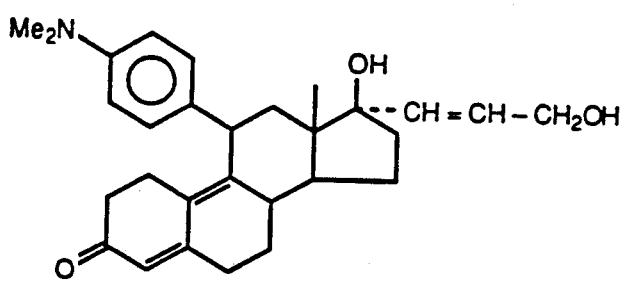
II
(ZK 98.734)
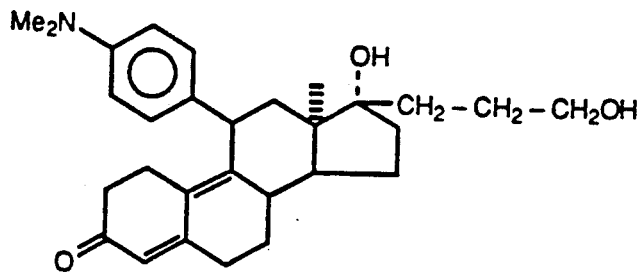
III
(ZK 98.299)
FIGURE 1. Chemical Structure of Some Investigated Antiprogestational Compounds

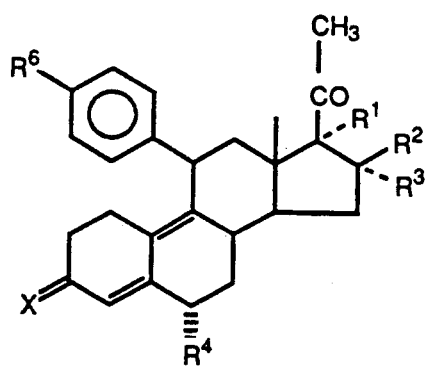
IV
FIGURE 2. Structure of Compounds of This Invention
($R^1 - R^6$ and X are Defined in the Text)

11β-SUBSTITUTED PROGESTERONE ANALOGS

This is a division of application Ser. No. 07/210,503, filed on June 23, 1988, now U.S. Pat. No. 4,954,490.

BACKGROUND OF THE INVENTION

1. Field of the Invention

This invention relates generally to the field of steroids, and in particular, to new 11β-substituted 19-norprogesterone analogs which possess antiprogestational or progestational activity.

2. Discussion of the Background

There have been many prior attempts over the past few decades to prepare steroids with antihormonal activity. These have been reasonably successful where anti-estrogens and anti-androgens are concerned. The discovery of effective antiprogestational and antiglucocorticoid steroids, however, has proved to be a formidable task for the steroid chemist. It has been generally recognized for some years, however, that antiprogestational steroids would find wide applicability in population control, while antiglucocorticoids would be extremely valuable in the treatment of, for example, Cushing's syndrome and other conditions characterized by excessive endogenous production of cortisone. In the last decade largely through the efforts of Teutsch et al of the Roussel-Uclaf group in France, a new series of 19-nortestosterone derivatives has been synthesized with strong affinity for the progesterone and glucocorticoid receptors and with marked antiprogestational and antiglucocorticoid activity in vivo. This important discovery revealed the existence of a pocket in the progesterone/cortisone receptors able to accommodate a large 11β-substituent on selected 19-nortestosterone derivatives. By suitable selection of such a substituent steroids with antihormonal properties were obtained.

The pioneering studies of Teutsch et al on the synthesis of antiprogestational and antiglucocorticoid steroids is summarized in a recent review (G. Teutsch in Adrenal Steroid Antagonism. Ed. M. K. Agarwal, Walter de Gruyter and Co., Berlin, 1984. pp. 43–75) describing work leading to the discovery of RU-38,486 (I), the first steroid of this type selected for clinical development. See FIG. 1. RU-38,486 or mefipristone was found to be an effective antiprogestational/contragestative agent when administered during the early stages of pregnancy (IPPF Medical Bulletin 20; No. 5, 1986). In addition to these antiprogestational properties, mefipristone had very significant antiglucocorticoid activity and was successfully used by Nieman et al (J. Clin. Endocrinology Metab. 61:536, 1985) in the treatment of Cushing's syndrome. In common with the vast majority of steroidal hormone analogs, mefipristone additionally exhibits a range of biological properties. Thus, for example, it exhibits growth-inhibitory properties towards estrogen-insensitive T47Dco human breast cancer cells (Horwitz, Endocrinology 116:2236, 1985). Experimental evidence suggests that the metabolic products derived from mefipristone contribute to its antiprogestational and antiglucocorticoid properties (Heikinheimo et al, J. Steroid Biochem. 26:279, 1987).

There have been a number of attempts by various workers to modify the mefipristone structure in order to obtain separation of the antiprogestational activity from the antiglucocorticoid activity. Thus, the Schering group (Steroids 44:349-519, 1984) has described analogs of mefipristone termed ZK 98.299 (II) and ZK 98.734 (III). See FIG. 1. Mefipristone is the most active antiglucocorticoid steroid relative to its antigestagenic potency while steroid (III) is the least active. Steroid (II) has an intermediate position in this respect.

Comparison of the contragestative properties of these three antiprogestational steroids (Elger et al., J. Steroid Biochem. 25:835, 1986) has not only revealed different endocrinological profiles, but has indicated the critical importance of the ratio of antiglucocorticoid to antiprogestational activity to the biological activity. It thus seems inevitable that a series of related structures possessing a gradation of antiprogestational/antiglucocorticoid properties will need to be developed in order to provide contragestative/antiglucocorticoid/antitumor products designed for specific clinical situations. Unfortunately, the art has not yet reached the stage when accurate predictions of biological properties on the basis of chemical structures can be made so that a degree of empiricism is unavoidable.

There continues to be a need for the development of new steroids with varying degrees of antiprogestational and antiglucocorticoid activities.

SUMMARY OF THE INVENTION

Accordingly, one object of the present invention is to provide new steroid compounds having anti-progestational and/or antiglucocorticoidal properties.

Another object of the invention is to provide novel steroids having progestational as well as antiprogestational activity.

These and other objects which will become apparent from the following specification have been achieved by the present 11β-aryl-19-norprogesterone compounds of the formula

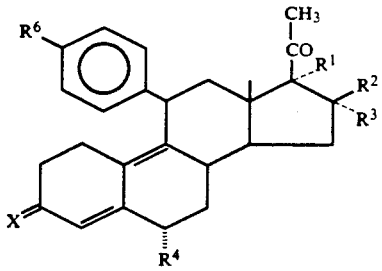

wherein (i) $R^1$ is H, $C_{1-4}$ alkyl, $C_{2-4}$ alkenyl, $C_{2-4}$ alkynyl, OH, $OC(O)CH_3$, or $OC(O)R^5$, wherein $R^5$ is $C_{2-8}$ alkyl, $C_{2-8}$ alkenyl, $C_{2-8}$ alkynyl or aryl, $R^2$ is H, $R^3$ is H, $C_{1-4}$ alkyl, $C_{2-4}$ alkenyl or $C_{2-4}$ alkynyl, $R^4$ is H, $CH_3$, F or Cl, $R^6$ is H, $(CH_3)_2N$, $CH_3O$, $CH_3CO$, $CH_3S$, $CH_3SO$ or $CH_3SO_2$ and X is O or $NOCH_3$; or (ii) $R^1$ and $R^2$ taken together represent a carbon-carbon bond, and $R^3$, $R^4$, $R^6$ and X are as defined above; or (iii) $R^1$ and $R^3$ taken together are $-CH_2-$ or $-N=N-CH_2-$, $R^2$ is H and $R^4$, $R^6$ and X are as defined above; or (iv) $R^2$ and $R^3$ taken together are $=CH_2$ and $R^1$, $R^4$, $R^6$ and X are as defined above.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 gives the structures of prior art compounds ZK 95.890, ZK 98.734 and ZK 98.299; and FIG. 2 illustrates the structures of the compounds of the present invention.

DETAILED DESCRIPTION OF THE PREFERRED EMBODIMENTS

Research in this area has dealt with 11β-aryl-19-nortestosterone analogs in which the 17β-position (or the 17α-position in the inverted compounds such as III) is substituted by a hydroxyl group. This invention provides for the first time novel 11β-aryl-19-norprogesterone analogs in which the 17β-position is substituted by an acetyl group. The resulting compounds are generally characterized by strong binding affinity to the progesterone and glucocorticoid receptors. Research in this series of structures, however, is not yet able to predict the nature of this biological activity on the basis of structure and binding affinity to the progesterone and glucocorticoid receptors. Thus in contrast to prior art which teaches that in the 11β-aryl-19-nortestosterone series, an 11β-aryl substituent, e.g. 11β-(4-N,N-dimethylaminophenyl), leads to antiprogestational activity, surprisingly in the 11β-aryl-19-norprogesterones of the present invention, strong binding to the progesterone receptor may lead to either antiprogestational or progestational activity in vivo. Thus the 17α-acetoxy structures IV (FIG. 2) ($R^1$=OAc, $R^2$=$R^3$=H, $R^4$=H or $CH_3$, $R^6$=$Me_2N$, X=O) and the 16α-ethyl structures IV ($R^1$=$R^2$=H, $R^3$=Et, $R^4$=H or $CH_3$, $R^6$=$Me_2N$, X=O) both exhibit strong binding to the progesterone receptor. The former compounds block the action of progesterone when administered in vivo, whereas the latter surprisingly show potent progestational activity in vivo.

Furthermore in the 19-norprogesterone series there is not always the expected correlation between binding to the progesterone receptor and in vivo activity. Thus the Δ-16 compound IV ($R^1$,$R^2$=double bond, $R^3$=$R^4$=H, $R^6$=$Me_2N$, X=O) binds relatively weakly to the progesterone receptor, but when used in vivo exhibits strong antiprogestational activity.

The 11β-substituted norprogesterone analogs of the present invention comprise compounds having structures A-C shown below.

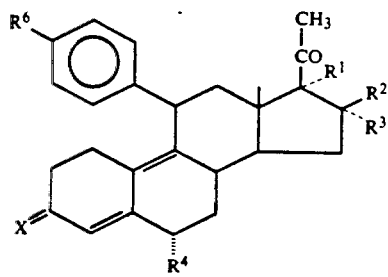

A

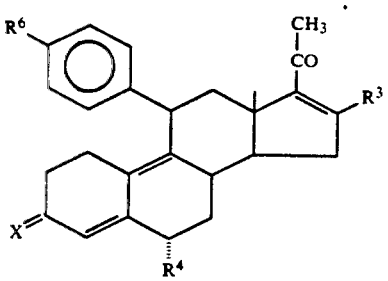

B

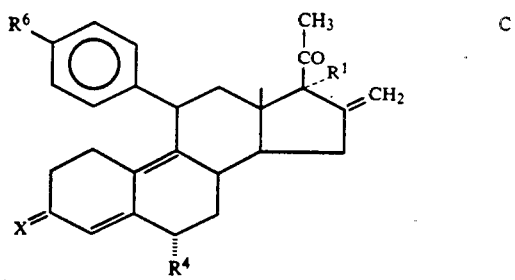

C

The compounds having structure A all contain a 16β-hydrogen substituent ($R^2$) and a 17β-acetyl substituent. The 16α substituent ($R^3$) may be hydrogen, $C_{1-4}$ alkyl, $C_{2-4}$ alkenyl or $C_{2-4}$ alkynyl groups. The 17α substituent ($R^1$) may be methyl, $C_{2-4}$ alkyl, $C_{2-4}$ alkenyl, $C_{2-4}$ alkynyl, hydroxyl, $OC(O)CH_3$ (O-acetyl), or OC(O)$R^5$, where $R^5$ is $C_{2-8}$ alkyl, $C_{2-8}$ alkenyl, $C_{2-8}$ alkynyl or aryl. Alternatively, the 17α- and 16α-substituents $R^1$ and $R^3$ taken together are —$CH_2$— or —N=N—$CH_2$—.

Preferred compounds having structure A are those in which $R^6$ is N,N-dimethylamino or acetyl. Additional preferred compounds are those in which $R^4$ is hydrogen or methyl and $R^1$ is acetoxy or $C_{2-6}$ alkynyl groups. Specific examples of compounds having structure A are 17α-acetoxy-6α-methyl-11β-(4-N,N-dimethylaminophenyl)-19-norpregna-4,9-diene-3,20-dione, 17α-acetoxy-11β-(4-N,N-dimethylaminophenyl)-19-norpregna-4,9-diene-3,20-dione, 16α-ethyl-11β-(4-N,N-dimethylaminophenyl)-19-norpregna-4,9-diene-3,20-dione, 16α-ethyl-6α-methyl-11β-(4-N,N-dimethylaminophenyl)-19-norpregna-4,9-diene-3,20-dione, 17α-ethynyl-11β-(4-N,N-dimethylaminophenyl)-19-norpregna-4,9-diene-3,20-dione, 11β-(4-N,N-dimethylaminophenyl)-19-norpregna-4,9-diene-3,20-dione, 11β-(4-acetylphenyl)-19-norpregna-4,9-diene-3,20-dione, 17α-acetoxy-11β-(4-acetylphenyl)-19-norpregna-4,9-diene-3,20-dione, and 17α-ethynyl-11β-(4-acetylphenyl)-19-norpregna-4,9-diene-3,20-dione.

Compounds having structure B exhibit a carbon-carbon double bond between C16 and C17. $R^3$, $R^4$, $R^6$ and X may be any of the groups defined above. Preferred compounds having structure B are compounds in which $R^6$ is an N,N-dimethylamino or an acetyl group. Additionally preferred compounds having structure B are those in which $R^3$ is H and $R^4$ is H or $CH_3$. Specific examples of such compounds include 11β-(4-N,N-dimethylaminophenyl)-19-norpregna-4,9,16-triene-3,20-dione and 11β-(4-acetylphenyl)-19-norpregna-4,9,16-triene-3,20-dione.

In the compounds having structure C, $R^2$ and $R^3$, taken together, are a =$CH_2$ group. Preferred examples include compounds in which $R^1$ is acetoxy or $C_{2-8}$ alkynyl, $R^4$ is hydrogen or methyl and $R^6$ is dimethylamino or acetyl.

Preferred aryl groups for $R^5$ in compounds A-C have the formula —$C_6H_4$—$R^6$, in which $R^6$ has the same meaning as defined above.

Steroids having progestational, antiprogestational and/or antiglucocorticoid activity have use in the control of fertility in humans and non-human mammals such as primates, domestic pets and farm animals, and in the treatment of medical conditions in animals or humans in which these activities are beneficial. Thus they may be useful in the treatment of conditions such as Cushing's syndrome, glaucoma, endometriosis, premenstrual syndrome and cancer in addition to their use in the control of reproduction.

The compounds of the present invention may be administered by a variety of methods. Thus, those products of the invention that are active by the oral route may be administered in solutions, suspensions, emulsions, tablets, including sublingual and intrabuccal tablets, soft gelatin capsules, including solutions used in soft gelatin capsules, aqueous or oil suspensions, emulsions, pills, lozenges, troches, tablets, syrups or elixirs and the like. Products of the invention active on parenteral administration may be administered by depot injection, implants including Silastic TM and biodegradable implants, intramuscular and intravenous injections.

Compositions may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension may also contain one or more preservatives such as ethyl or n-propyl p-hydroxybenzoate, one or more coloring agents, one or more flavoring agents and one or more sweetening agents, such as sucrose, aspartame or saccharin. Ophthalmic formulations, as is known in the art, will be adjusted for osmotic pressure.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the invention suitable for preparation of an aqueous suspension by the addition of water may be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally-acceptable diluent or solvent, such as a solution of 1,3-butanediol. Among the acceptable vehicles and solvents that may be employed are water and Ringer's solution, an isotonic sodium chloride. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The compounds of this invention may also be administered in the form of suppositories for rectal administration of the drug. These compositions can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

They may also be administered by intranasal, intraocular, intravaginal, and intrarectal routes including suppositories, insufflation, powders and aerosol formulations.

Products of the invention which are preferably administered by the topical route may be administered as applicator sticks, solutions, suspensions, emulsions, gels, creams, ointments, pastes, jellies, paints, powders, and aerosols.

Products having anti-glucocorticoid activity are of particular value in pathological conditions characterized by excess endogenous glucocorticoid such as Cushing's syndrome, hirsutism and in particular when associated with the adrenogenital syndrome, ocular conditions associated with glucocorticoid excess such as glaucoma, stress symptoms associated with excess glucocorticoid secretion and the like.

Products having progestational activity are of particular value as progestational agents, ovulation inhibitors, menses regulators, contraceptive agents, agents for synchronization of fertile periods in cattle, endometriosis, and the like. When used for contraceptive purposes, they may conveniently be admixed with estrogenic agents, such as for example as ethynylestradiol or estradiol esters.

Products having anti-progestational activity are characterized by antagonizing the effects of progesterone. As such, they are of particular value in control of hormonal irregularities in the menstrual cycle and for synchronization of fertile periods in cattle.

The compounds of the invention may be used for control of fertility during the whole of the reproductive cycle. They are of particular value as postcoital contraceptives, for rendering the uterus inimical to implantation, and as "once a month" contraceptive agents. They may be used in conjunction with prostaglandins, oxytocics and the like.

A further important utility for the products of the invention lies in their ability to slow down growth of hormone-dependent cancers. Such cancers include kidney, breast, endometrial, ovarian cancers, and prostate cancer which are characterized by possessing progesterone receptors and may be expected to respond to the products of this invention. Other utilities of anti-progestational agents include treatment of fibrocystic disease of the breast. Certain cancers and in particular melanomas may respond favorably to corticoid/anticorticoid therapy.

The compounds according to the present invention may be administered to any warm-blooded mammal such as humans, domestic pets, and farm animals. Domestic pets include dogs, cats, etc. Farm animals include cows, horses, pigs, sheep, goats, etc.

The amount of active ingredient that may be combined with a carrier material to produce a single dosage form will vary depending upon the disease treated, the mammalian species, and the particular mode of administration. For example, a unit dose of the steroid may preferably contain between 0.1 milligram and 1 gram of the active ingredient. A more preferred unit dose is between 0.001 and 0.5 grams. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the art.

Other features of the invention will become apparent in the course of the following descriptions of exemplary embodiments which are given for illustration of the invention and are not intended to be limiting thereof.

EXAMPLES

EXAMPLE 1

Synthesis of 6α-Methyl-17α-acetoxy-11β-(4-N,N-dimethylaminophenyl)-19-norpregna-4,9-diene-3,20-dione 6α-Methyl-17α-hydroxy-pregna-1,4-diene-3,20-dione (37.72 g, 0.11 mol) was dissolved in 1 L of freshly distilled tetrahydrofuran and 400 mL of dry methanol. The solution was cooled in an ice-bath at 0° C. Sodium borohydride (3.6 g, 0.09 mol) was added in one portion and the mixture was stirred at 0°–5° C. for 6 h. The reaction mixture was diluted with ice water (100 mL) and methanol was removed under reduced pressure. The resulting thick residue was partitioned between chloroform and water. The chloroform extracts (500 mL×4) was dried over $Na_2SO_4$ (anhydrous), filtered and concentrated to give 42 g of crude 6α-methyl-17α,20β(α)- dihydroxy-pregna-1,4-dien-3-one. The product was shown to be a mixture of 20β and 20α-ol in a ratio of 85:15 based on $^1H$ NMR analysis. For 20β-ol: $^1H$ NMR ($CDCl_3$, 60 MHz) δ 0.83 (s, 3, 18-$CH_3$), 1.0 (d, 3, J=6 Hz, 6-$CH_3$), 1.18 (d, 3, J=6 Hz, 21—$CH_3$), 4.0 (m, 1, 20-H), 6.05 (bs, 1, 4-H), 6.15 (dd, 1, J=12, 2 Hz, 2-H), 7.1 (d, 1, J=12 Hz, 1-H).

Into a flame dried 2 L three-neck round bottom flask equipped with condenser and addition funnel were added tetrahydrofuran (900 mL), biphenyl (45 g, 0.29 mol) and diphenylmethane (50 mL, 0.285 mol). The mixture was heated to reflux and lithium wire (3.5 g, 0.50 mol) was added in one portion. The resulting bluish-green solution of the complex was heated at gentle reflux for 16 h. An additional 0.5 g of lithium wire was added to maintain a dark-blue color. The diol (26 g, 0.076 mol) in 170 mL of THF was then added dropwise at such a rate that the blue color persisted throughout the addition. The reaction mixture was refluxed for an additional 45 min. The excess biphenyl lithium complex was quenched carefully with methanol in an ice-bath. After dilution with water (200 mL), THF was removed under reduced pressure and the product was extracted with $CHCl_3$ (500 mL×3). The $CHCl_3$ extracts were combined, dried over sodium sulfate (anhydrous), filtered and concentrated to give 118 g of the crude product. The aqueous phase was acidified with HCl solution (10% v/v) and extracted with $CHCl_3$ (500 mL×2). The $CHCl_3$ extract was dried over $Na_2SO_4$ (anhydrous), filtered and concentrated to give 4.5 g of fairly pure 6α-methyl-19-norpregna-1,3,5(10)-triene- 3,17α,20β(α) -triol. The 118 g of crude reaction product was purified by $SiO_2$ column chromatography employing a gradient system (n-hexane-$CH_2Cl_2$ to 5% acetone-$CH_2Cl_2$) to give another 11.2 g of the product: mp=175°–179° C.; $^1H$ NMR (250 MHz, $CDCl_3$) δ 0.82 (s, 3, 18-$CH_3$), 1.17 (d, 3, J=6.4 Hz, 21-$CH_3$), 1.28 (d, 3, J=6.8 Hz, 6α-$CH_3$), 4.0 (m, 1, 20-H), 6.61 (dd, 1, J=8.5, 2.6 Hz, 2-H), 6.76 (d, 1, J=2.6 Hz, 4-H), 7.11 (d, 1, J=8.5 Hz, 1-H); calcd. mass for $C_{21}H_{30}O_3$: 330,2095, Found: 330.2197.

Anal. Calcd for $C_{21}H_{30}O_3$: C. 76.32; H. 9.15. Found: C, 76.82; H, 9.40.

The above crude phenolic product (6.5 g, 0.02 mol) was dissolved in 500 mL of methanol and treated with potassium carbonate (15.0 g, 0.10 mol) and iodomethane (20 mL, 0.32 mol). The mixture was stirred at room temperature for 48 hours. Methanol was removed under reduced pressure, the residue was diluted with water and acidified with 10% (v/v) HCl solution. The product was extracted with CHCl$_3$ (300 mL×3). The combined CHCl$_3$ extract was washed with water, dried over sodium sulfate (anhydrous), filtered and concentrated to give 7.0 g of crude reaction product. SiO$_2$ column chromatography (CH$_2$Cl$_2$ to 5% acetone-CH$_2$Cl$_2$) gave three fractions: Fraction A (4.0 g) was found to be 6α-methyl-3-methoxy-19-norpregna-1,3,5(10)-triene-17α,20β(α)- diol. Fraction B (0.74 g) was found to be its 20α-hydroxy isomer and Fraction C (0.54g) was the recovered starting phenol. For the 20β-ol: mp=145°-147° C.; $^1$H NMR (250 MHz, CDCl$_3$) δ 0.82 (s, 3, 18-CH$_3$), 1.20 (d, 3, J=6.3 Hz, 21-CH$_3$), 1.30 (d, 3, J=7.0 Hz, 6α-CH$_3$), 2.79 (s, 3, OCH$_3$), 4.06 (m, 1, 20-H), 6.73 (dd, 1, J=8.7, 2.7 Hz, 2-H), 6.82 (d, 1, J=2.7 Hz, 4-H), 7.20 (d, 1, J=8.7 Hz, 1-H); Calcd mass for C$_{22}$H$_{32}$O$_3$: 344.2355. Found 344.2355. Anal. Calcd for C$_{22}$H$_{32}$O$_3$: C, 77.16; H, 8.83. Found: C, 77.14: H, 8.88. For 20α-ol: mp=150°-151° C.; $^1$H NMR (250 MHz, CDCl$_3$) δ 0.75 (s, 3, 18-CH$_3$), 1.22 (d, 3, J=6.4 Hz, 21-CH$_3$), 1.30 (d, 3, J=6.9 Hz, 6α-CH$_3$), 3.79 (s, 3, OCH$_3$), 3.85 (m, 1, 20-H), 6.70 (dd, J=8.7, 2.7 Hz, 2-H), 6.82 (d, 1, J=2.7 Hz, 4-H), 7.20 (d. 1. J=8.6 Hz, 1-H).

Liquid ammonia (35 mL) was condensed into a flame dried three-neck round bottom flask equipped with a Dewar condenser and an additional funnel. Lithium wire (150 mg, 21.6 mmol) was added and the resulting bluish solution of the Li/NH$_3$ complex solution was stirred at −78° C. for 1 hour. The above methyl ether (380 mg. 1.11 mmol) in 2.0 mL of dry THF and 1.0 mL of t-butanol was added dropwise. The blue color persisted throughout the addition. The resulting mixture was stirred at −78° C. for an additional 45 minutes and quenched carefully with methanol until the blue color faded. Excess ammonia was evaporated under a slow stream of nitrogen. The residue was diluted with water and neutralized with 10% (v/v) HCl solution. The product was extracted with CHCl$_3$ (50 mL×3). The CHCl$_3$ extract was dried over Na$_2$SO$_4$ (anhydrous), filtered and concentrated to give 380 mg of crude 6α-methyl-3-methoxy-19-norpregna-2,5(10)-diene-17α,20β-diol. $^1$H NMR (60 MHz) δ 0.80 (s, 3, 18-CH$_3$), 1.0 (d, 3, J=6.4 Hz, 6α-CH$_3$), 1.2 (d, J=6 Hz, 21-CH$_3$), 3.5 (s, 3, 3-OCH$_3$), 4.0 (m, 1, 20-H), 4.6 (bs, 1, 2-h).

Without further purification the crude Birch reduction product was dissolved in 40 mL of methanol and treated with oxalic acid (250 mg in 1.5 mL of H$_2$O). The mixture was stirred at room temperature for 5 hours and then solvent removed under pressure and the product extracted with CHCl$_3$ (50 mL×3). The CHCl$_3$ extract was dried over Na$_2$SO$_4$ (anhydrous), filtered and concentrated to give 350 mg of the crude hydrolyzed product. Column chromatography (SiO$_2$; gradient from CH$_2$Cl$_2$ to 5% acetone CH$_2$Cl$_2$) gave 120 mg of 6α-methyl-17α,20β-dihydroxy-19-norpregn-5(10)-en-3-one: $^1$H NMR (250 MHz, CDCl$_3$) δ 0.82 (s, 3, 18-CH$_3$), 0.99 (d, 3, J=6.9 Hz, 6α-CH$_3$, 1.18 (d, 3, J=6.2 Hz, 21-CH$_3$), 2.4 (bs, 2, 4-H). 4.0 (m. 1. 20-H).

Purified 6α-methyl-17α,20β-dihydroxy-19-norpregna-5(10)-en-3-one (8.31 g, 0.025 mol) in 450 mL of dry pyridine was cooled in an ice bath and treated with pyridinium hydrobromide perbromide (9.30 g, 0.028 mol). After the mixture was stirred at room temperature for 24 hours, it was poured into ice-cold sodium sulfite solution (500 mL, 10% w/v) and extracted with CHCl$_3$ (400 mL×3). The CHCl$_3$ extract was washed with dilute NaHCO$_3$ solution (5% w/v), dried over Na$_2$SO$_4$ (anhydrous), filtered and concentrated to give 8.5 g of crude reaction product. Column chromatography (SiO$_2$; gradient from CH$_2$Cl$_2$ to 5% acetone in CH$_2$Cl$_2$) gave 5.8 g of 6α-methyl-17α,20β-dihydroxy-19-norpregna-4,9-dien-3-one: mp=201°-203° C.; $^1$H NMR (250 MHz, CDCl$_3$), δ 0.97 (s, 3, 18-CH$_3$); 1.13 (d, J=6.5 Hz, 6α-CH$_3$), 1.19 (d, 3, J=6.2 Hz, 21-CH$_3$), 4.08 (m, 1, 20-H), 5.8 (bs, 1, 4-H), IR (CHCl$_3$) 3550-3400; (—OH), 1665 (conjugated 3-C=O) cm$^{-1}$; UV (MeOH) λ$_{max}$305 nm; MS Calcd mass for C$_{21}$H$_{30}$O$_3$ 330.2195; Found 330.2194; Anal. Calcd for C$_{21}$H$_{30}$O$_3$; C, 76.33; H, 9.15. Found: C, 76.35; H, 9.17.

To a stirred solution of CH$_2$Cl$_2$ (150 ml) and oxalyl chloride (4.5 mL, 0.050 mol) was added DMSO (9.0 mL, 0.12 mol at −60° C. in a dry ice-CHCl$_3$ bath. The mixture was stirred for 5 min and the above compound (5.7 g, 0.017 mol) in 60 mL of methylene chloride was added during 5 min; stirring was continued for an additional 30 min. Triethylamine (25 mL, 0.175 mol) was added and the reaction mixture was stirred for 15 min and then allowed to warm briefly to room temperature. Water (150 mL) was then added and the aqueous layer was reextracted with CH$_2$Cl$_2$ (300 mL×2). The organic layers were combined, washed with saturated NaCl solution, dried, filtered and concentrated to give 5.8 g of crude reaction product. Column chromatography (SiO$_2$; CH$_2$C$_{12}$→10% acetone in CH$_2$Cl$_2$) provided 5.1 g of 6α-methyl-17α-hydroxy-19-norpregna-4,9(10)-diene-3,20-dione. Recrystallization from MeOH gave white crystals: mp=230°-232° C.; $^1$H NMR (CDCl$_3$, 60 MHz) δ 0.78 (s, 3, 18-CH$_3$), 1.10 (d, 3, J=6.5 Hz, 6α-CH$_3$), 2.25 (s, 3, 21-CH$_3$), 5.8 H), IR (CHC$_{13}$) 1700 (20-C=0), 1665 (conjugated 3-C=O) cm$^{-1}$; UV (MeOH) λ$_{max}$305 nm; Calcd mass for C$_{21}$H$_{28}$O$_3$; 328.2038. Found: 328.2038; Anal. Calcd for C$_{21}$H$_{28}$O$_3$: C, 76.79; H, 8.59. Found: C, 76.87; H, 8.64.

To a solution of the above dione (5.8 g, 0.018 mol) in 450 mL of dry benzene was added ethylene glycol (24.0 mL) and p-toluenesulfonic acid (500 mg). The mixture was heated to reflux and a total of 150 mL of benzene was distilled off over a period of 3 h. The reaction mixture was poured over ice water and extracted with ethyl acetate (300 mL×3). The organic phase was washed with water, dried over sodium sulfate (anhydrous), filtered and concentrated. The crude residue was chromatographed over SiO$_2$ (100% CH$_2$Cl$_2$→2% acetone-CH$_2$Cl$_2$) to give 4.6 g of 6α-methyl-3,3,20,20-bis-(ethylenedioxy)-19-norpregna-5(10),9(11)-dien-17α-ol together with 1.0 g of 6β-methyl-3,3,20,20-bis-(ethylenedioxy)-19-norpregna-5(10),9(11)-dien-17α-ol. For the 6α-methyl-3,20-diketal: mp=157°-158° C.; $^1$H NMR (CDCl$_3$, 250 MHz) δ 0.78 (s, 3, 18-CH$_3$); 0.99 (d, 3, J=6.8 Hz, 6α-CH$_3$), 1.37 (s, 3, 21-CH$_3$), 3.98 (m, 8, 3,3,20,20-bisketals), 5.57 (bs, 1, 11-H), Calcd mass for C$_{25}$H$_{36}$O$_5$: 416.2563. Found 416.2564; Anal. Calcd for C$_{25}$H$_{36}$O$_5$: C, 72.08; H, 8.71. Found: C, 72.14; H, 8.75.

To a solution of the above bisketal (3.2 g, 7.7 mmol) in 75 mL of methylene chloride/hexane (1:3) was added m-chloroperbenzoic acid (1.62 g, 80%) at 0° C. The mixture was stirred at 0° C. for 10 min and then diluted with sodium bicarbonate solution (25 mL, 5% w/v). The aqueous phase was extracted with CH$_2$Cl$_2$ (50 mL×2). The combined organic phase was washed with saturated sodium chloride solution, dried over sodium sulfate (anhydrous), filtered and concentrated to give 3.4 g of crude epoxides which consisted mainly of 5α,10α-epoxide as revealed by TLC and $^1$H NMR analyses: $^1$H NMR (CDCl$_3$, 60 MHz) δ 0.75 (s, 3, 18-CH$_3$), 0.95 (d, 3, J=6.0 Hz, 6α-CH$_3$), 1.30 (s, 3, 21-CH$_3$), 3.8-4.0 (m, 8, 3, 20-ketals), 5.8 (m, 1, 11-H).

The crude epoxide (3.4 g, 7.43 mmol) in dry tetrahydrofuran (25 mL) was added dropwise to a Grignard solution of p-N,N-dimethylaminophenylmagnesium bromide in the presence of dimethylsulfide cuprous bromide complex (1.8 g. 8.6 mmol). The Grignard mixture was prepared from p-bromo-N,N-dimethylaniline (14.0 g, 70 mmol) and magnesium (1.4 g, 57 mmol) in 150 mL of freshly distilled tetrahydrofuran. After the reaction mixture was stirred at room temperature and under nitrogen for 30 min., it was poured into saturated ammonium chloride solution (350 mL) and stirred for 20 min. Extraction with ethyl acetate (500 mL×3) and evaporation of the solvent gave a bluish residue which was first purified by $Al_2O_3$ column chromatography to provide 3.7 g of semi-purified product. Repeated silica gel column chromatography yielded 1.95 g of 6α-methyl-11β-(4-N,N-dimethylaminophenyl)-3,3,20,20-bis(ethylenedioxy)-19-norpregn-9-en-5α-ol. Recrystallization from $MeOH/CH_2Cl_2$ gave 1.2 g of needles: mp=227°-228° C.; 1H NMR (250 MHz, $CDCl_3$) δ 0.46 (s, 3, 18-$CH_3$), 1.06 (d, 3, J=6.6 Hz, 6α-$CH_3$), 1.38 (s, 3, 21-$CH_3$), 2.89 (s, 6, —N($CH_3$)$_2$), 3.8-4.0 (m, 8, 3, 20-diethylene ketal-H), 4.19 (d, 1, J=6.2 Hz, 11β-H), 6.62 (d, 2, J=8.8 Hz, aromatic H ortho to —N($CH_3$)$_2$), 7.06 (d, 2, J=8.8 Hz, aromatic-H, meta to -N($CH_3$)$_2$); Calcd for $C_{33}H_{47}O_6N$: C, 71.58; H, 8.56; N, 2.53. Found: C, 71.70; H, 8.59; N, 2.51.

Phosphoric acid (85%, 6.5 mL) was added dropwise into acetic anhydride (18 mL) in an ice-bath. The mixture was stirred at 5°-10° C. for 30 min and diluted with acetic acid (20 mL). The resulting mixture was warmed to room temperature and stirred for 1 hour. The above 17α-hydroxy-3,20-diketal (680 mg, 1.52 mmol) in dry dioxane (4.0 mL) was added to the phosphoric acid/acetic anhydride/acetic acid solution (8.0 mL). The mixture turned immediately into a dark-blue solution. The progress of the acetylation was carefully monitored with reverse phase-HPLC analyses. The reaction was stirred at room temperature for 8 hours and diluted with water followed by neutralization with sodium bicarbonate solution (5% w/v). The product was extracted with ethyl acetate (200 mL×3). The organic phase was dried over sodium sulfate (anhydrous), filtered and concentrated to give 750 mg of crude reaction product which was purified by $Al_2O_3$ column chromatography followed by repeated reverse-phase column chromatography employing a RP-$C_8$ (Lobar size B) column and 20% $H_2O$ in MeOH as the eluting solvent system. Each individual fraction collected was monitored by an analytical Zorbax-ODS (4.5 mm×25 cm) column with the same solvent system. The fractions showing greater than 95% purity were combined and solvent was evaporated. Further recrystallization from MeOH/$H_2O$ provided 110 mg of white crystals of 6α-methyl-17α-acetoxy-11β-(4-N,N-dimethylaminophenyl)-19-norpregna-4,9-diene-3,20-dione. The major contaminant found both in the mother liquor and in the overlapping fractions was the 6β-methyl isomer. For the 6α-methyl isomer: mp=189°-190.5° C.; 1H NMR (250 MHz, $CDCl_3$) δ 0.35 (s, 3, 18-$CH_3$), 1.24 (d, 3, J=6.5 Hz, 6α-$CH_3$), 2.09 (s, 3, 17α-OAc), 2.12 (s, 3, 21-$CH_3$), 2.9 (s, 6, —N($CH_3$)$_2$), 4.40 (d, 1, J=7.2 Hz, 11α-H), 5.89 (bs, 1, 4-H), 6.62 (d, 2, J=8.8 Hz aromatic-H, ortho to —N($CH_3$)$_2$), 6.96 (d, 2, J=8.8 Hz aromatic-H, meta to —N($CH_3$)$_2$); Calcd mass for $C_{31}H_{39}O_4N$: 489.2879. Found 489.2878; IR ($CHCl_3$), 1730 (17α-C=O), 1720 (20-C=O), 1655 (conjugated 3-C=O) cm$^{-1}$; UV (MeOH) $\lambda_{max}$ 302 nm (dienone), 264 nm (aromatic group); Anal. calcd for $C_{31}H_{39}O_4N$: C, 76.04; H, 8.02; N, 2.86. Found: C, 76.10; H, 8.03; N, 2.84.

EXAMPLE 2

Synthesis of
17α-Acetoxy-11β-(4-N,N-dimethylaminophenyl)-19-norpregna-4,9-diene-3,20-dione 3-Methoxy-19-norpregna-1,3,5(10),17(20)-tetrene (Krubiner and Oliveto, 1966) (1.0 g, 0.0034 mol) in dry pyridine (15 mL) was treated with osmium tetroxide (1.0 g). The resulting dark brown solution was stirred at room temperature for 2 hours and a solution of sodium bisulfite (1.8 g in 30 mL $H_2O$) and pyridine (20 mL) was added and the mixture was stirred for a additional 15 min.

The product was extracted with ethyl acetate and the combined organic phase was washed with water, dried over sodium sulfate (anhydrous), filtered and concentrated. Flash chromatography ($SiO_2$; 10% acetone in $CH_2Cl_2$) provided 0.82 g of 3-methoxy-19-norpregna-1,3,5(10)-triene-17α,20β-diol: 1H NMR ($CDCl_3$, 250 mHz) δ 0.76 (s, 3, 18-$CH_3$), 1.23 (d, 3, J=6.3 Hz, 21-H), 3.77 (s, 3, OMe), 3.87 (q, 1, J=6.3 Hz, 20-H), 6.62 (d, 1, J=2.8 Hz. 4-H), 6.70 (dd, 1, J=8.5. 2.8 Hz, 2-H), 7.20 (d, 1, J=8.5 Hz, 1-H).

By reduction with lithium in ammonia followed by oxalic acid treatment as described in Example 1, the above methyl ether (760 mg) was converted to 3-methoxy-19-norpregna-2,5(10)-diene-17α,20β-diol and thence to 17α,20α-dihydroxy-19-nor-5(10)-pregnen-3-one. 1H NMR (90 MHz, $CDCl_3$), δ 0.80 (s, 3, 18-$CH_3$), 1.2 (d, 3, J=6.5 Hz. 21-H), 2.4 (bs, 2, 4-H), 4.0 (m, 1, 20-H).

Pyridinium hydrobromide perbromide (1.5 mmol) as in Example 1, converted this compound to 230 mg of 17α,20(α)-dihydroxy-19-norpregna-4,9-dien-3-one. 1H NMR ($CDCl_3$, 90 MHz) δ 0.95 (s, 3, 18-$CH_3$), 1.15 (d, 3, J=6.5 Hz, 21-H), 4.1 (m, 1, 20-H), 5.7 (s, 1, 4-H).

Oxidation of the above diol (210 mg) with oxalyl chloride and dimethylsulfoxide as in Example 1 gave 17α-hydroxy-19-norpregna-4,9-diene-3,20-dione: 1H NMR ($CDCl_3$, 90 MHz) δ 0.87 (s, 3, 18-$CH_3$), 2.25 (s, 3, 21-H), 5.70 (bs, 1, 4-H); IR ($CHCl_3$) 1700 (20-C=O), 1665 (conjugated 3-C=O) cm$^{-1}$. This compound was converted to 190 m9 of 3,3,20,20-bis-(ethylenedioxy)-19-norpregna-5(10),9(11)-dien-17α-ol by the procedure described in Example 1: 1H NMR ($CDCl_3$, 90 MHz) δ 1.35 (s, 3, 21-H), 0.80 (s, 3, 18-$CH_3$), 3.98 (m, 8, 3,20-ketals), 5.6 (bs, 1, 11-H).

The above bisketal (175 mg) was epoxidized with meta-chloroperbenzoic acid by the procedure of Example 1 to yield crude 5α,10α-epoxy-3,3,20,20-bis-(ethylenedioxy)-19-norpregn-9(11)-en-17α-ol (25) which underwent copper catalyzed Grignard addition as in Example 1 to provide 100 mg of 3,3,20,20-bis(ethylenedioxy)-11β-(4,N,N-dimethylaminophenyl)-19-norpregn-9-ene-5α,17α-diol: 1H NMR ($CDCl_3$, 90 MHz) δ 0.46 (s, 3, 18-$CH_3$), 1.38 (s, 3, 21-H), 2.89 (s, 6, —N($CH_3$)$_2$), 3.8 (m, 8, 3,20-ketals), 4.78 (bt, 1, 11α-H), 6.6-7.1 (m, 4, aromatic-H).

Treatment of this compound with acetic anhydride/phosphoric acid as described in Example 1 yielded 17α-acetoxy-11β-(4-N,N-dimethylaminophenyl)-19-norpregna-4,9-diene-3,20-dione which was recrystallized from MeOH/$H_2O$ to give 25 mg of the final product: mp=118°-121° C.; 1H NMR ($CDCl_3$, 250 MHz) δ 0.36 (s, 3, 18-$CH_3$), 2.09 (s, 3, 17α-OAc), 2.13 (s, 3, 21-$CH_3$), 2.9 (s, 6, —N(CH$_3$)$_2$), 4.39 (d, 1 J=7.0 Hz, 11α-H), 5.77 (s, 1, 4-H), 6.6 (d, 2, J=8.6 Hz, aromatic ortho-H to —N(CH$_3$)$_2$), 6.9 (d, 2, J=8.6 Hz, aromatic meta-H to N(CH$_3$)$_2$; IR (CHCl$_3$) 1730 (20-C=O), 1660 (3-conjugated C=O) cm$^{-1}$; UV (MeOH), $\lambda_{max}$, 261 nm; Anal. Calcd. for C$_{30}$H$_{37}$NO$_4$: C, 75.76; H, 7.84; N, 2.94. Found: C, 74.18; H, 7.75; N, 2.81.

EXAMPLE 3

Synthesis of 6α-Methyl-16α-ethyl-11β-(4-N,N-dimethylaminophenyl)-19-norpregna-4,9-diene-3,20-dione 6α-Methyl-3-methoxy-19-norpregna-1,3,5(10)-triene-17α,20β-diol (900 mg, 2.6 mmol) in 30 mL of THF was treated with H$_5$IO$_6$ solution (400 mg in 10 mL THF). The reaction mixture was stirred at room temperature for 45 min and filtered through a short neutral alumina column. The filtrate and THF washings were combined and concentrated to give 750 mg of product. Recrystallization from methanol gave 450 mg of 3-methoxy-6α-methyl-1,3,5(10)estratrien-17-one: mp=108°-109° C.; $^1$H NMR (CDCl$_3$, 90 MHz) δ 0.88 (s, 3, 18-CH$_3$), 1.3 (d, 3, J=6.5 Hz, 6α-Me), 3.75 (s, 3, 3-OMe), 6.8°-7.2 (m, 3, aromatic H); IR (CHC$_{13}$) 1740 cm$^{-1}$ (17-C=O); Anal. calcd for C$_{20}$H$_{26}$O$_2$: C, 80.5; H, 8.78. Found: C, 80.59; H. 8.80.

A solution of the above 6α-methylestrone-3-methyl ether (5.2 g. 0.017 mol) in dry toluene was added rapidly to a stirred solution of ethylidenetriphenylphosphorane freshly prepared from 6.3 g of NaH in 100 mL of DMSO and ethyltriphenylphosphonium iodide (54.8 g, 0.13 mol). The reaction mixture was stirred at 60° C. for 18 hours and was then poured over ice. The product was taken up with ethyl acetate. The combined organic phase was dried over sodium sulfate, filtered, and concentrated to give 8.5 g of crude product which was purified by SiO$_2$ column chromatography (hexane—CH$_2$Cl$_2$, 1:1) to give 4.8 g of 3-methoxy-6α-methyl-19-norpregna-1,3,5(10),17(20)-tetraene. $^1$H NMR (CDCl$_3$, 90 MHz) δ 0.89 (s, 3, 18-CH$_3$) 1.3 (d, 3, J=6.5 Hz, 6α-CH$_3$), 1.6 (d, 3, J=7 Hz, 21-H), 3.8 (s, 3, OMe), 5.1 (m, 1, 20-H), 6.8-7.2 (m, 3, aromatic-H); IR (CHCl$_3$), no C=O.

A solution of the above olefin (500 mg, 1.61 mmol) and hematoporphyrin (22 mg) in 20 mL of pyridine was treated with a fine stream of oxygen while being illuminated with a 22 W fluorescent lamp. After 4.5 h, 5 mL of acetic anhydride was added and the reaction mixture was allowed to stand at room temperature for 45 min and was then heated at 60° C. for additional 30 min. After dilution with water, the product was extracted with methylene chloride and the organic phase washed thoroughly with 1N HCl and then with 5% sodium bicarbonate solution. After drying, the methylene chloride solution was slurried with 15 g of neutral alumina oxide and filtered. The concentrated crude reaction product was further purified by SiO$_2$ column chromatography (15% acetone in CH$_2$Cl$_2$) to provide 350 mg of 3-methoxy-6α-methyl-19-norpregna-1,3,5(10),16-tetraen-20-one: mp=106°-109° C.; $^1$H NMR (CDCl$_3$, 90 MHz), δ 0.90 (s, 3, 18-CH$_3$), 1.29 (d, 3, J=6.5 Hz, 6α-CH$_3$), 2.23 (s, 3, 21-H), 3.75 (s, 3, OMe), 6.7 (m, 3, 2, 4 16-H), 7.15 (d, 1, J=7 Hz, 1-H); IR (CHCl$_3$) 1670 (conjugated 20-C=O) cm$^{-1}$.

Ethylmagnesium bromide (12.5 mL, 25 mmol) 2 M in THF was added to a suspension of Me$_2$S.CuBr complex (2.4 g, 0.0177 mol) in 80 mL of THF at 0° C. under N$_2$. The resulting blue solution of the complex was stirred at 0° C. for 20 min and then was added to a cold solution of the above tetraene (1.5 g, 0.0046 mol) in 40 mL of THF. The reaction mixture was stirred for 30 min at 0° C. and then diluted with 1 N HCl solution (15 mL). The product was extracted with ethyl acetate. The organic phase was dried, filtered and concentrated to give 2.0 g of crude reaction product. Column chromatography (SiO$_2$; 2% acetone in CH$_2$Cl$_2$) provided 1.5 g of 3-methoxy-6α-methyl-16α-ethyl-19-norpregna-1,3,5(10)-trien-20-one; $^1$H NMR (CDCl$_3$, 250 MHz) δ 7.18 (d, 1, J=8.6 Hz, 1-H), 6.75 (m, 2, 2 4-H), 3.78 (s, 3, OMe), 2.15 (s, 3, 21-H), 1.30 (d, 3, J=6.8 Hz, 6α-CH$_3$), 0.85 (t, 3, J=7 Hz, 16-CH$_2$CH$_3$), 0.65 (s, 3, 18-CH$_3$); IR (CHC$_{13}$) 1702 (20-C=O) cm$^{-1}$.

The above 20-keto compound (7.0 g, 0.020 mol) in THF (250 mL) and methanol (80 mL) was cooled to 0° C. in an ice bath and treated with sodium borohydride (1.0 g, 0.027 mol). The mixture was stirred at 0° C. for 6.5 hours and was then poured carefully into crushed ice. The product was extracted with ethyl acetate. The organic extract was dried, filtered and concentrated to give 7.3 g of crude product which was purified by SiO$_2$ column chromatography (2% acetone in CH$_2$Cl$_2$) to provide 6.8 g of 3-methoxy-6α-methyl-16α-ethyl-19-norpregna-1,3,5(10)-trien-20β(α)-ol: $^1$H NMR (CDCl$_3$, 250 MHz) δ 0.82 (s, 3, 18-CH$_3$), 0.90 (t, 3, J=7.2 Hz, 16-CH$_2$CH$_3$), 1.22 (d, 3, J=6.3 Hz, 6α-CH$_3$), 1.30 (d, 3, J=6.8 Hz, 21-H), 2.9 (m, 1, 20-H), 3.78 (s, 3, 3-OMe), 6.7 (dd, 1, J=8.5, 2.7 Hz, 2-H), 6.8 (d, 1, J=2.7 Hz, 4-H), 7.20 (d, 1, J=8.5 Hz, 1-H).

By the lithium in liquid ammonia procedure of Example 1, the above steroid (4.0 g. 0.0113 mol) was converted to 3.95 g of crude 3-methoxy-6α-methyl-16α-ethyl-19-norpregna-2,5(10)-dien-20β(α)-ol which upon treatment with oxalic acid by the procedure in Example 1 provided 2.85 g of 6α-methyl-16α-ethyl-20β(α)-hydroxy-19-nor-5(10)-pregnen-3-one: $^1$H NMR (CDCl$_3$, 250 MHz) δ 0.82 (s, 3, 18-CH$_3$), 0.89 (t, 3, J=7.0 Hz, 16-CH$_2$CH$_3$), 1.0 (d, 3, J=6.9 Hz, 6α-CH$_3$), 1.20 (d, 3, J=6.2 Hz. 21-H). 3.8 (m. 1. 20-H).

Treatment of the latter (220 mg) with pyridinium hydrobromide perbromide by the procedure of Example 1 provided 22 mg of 20β-isomer and 150 mg of 20β-isomer of 20-hydroxy-6α-methyl-16α-ethyl-19-norpregna-4,9-dien-3-one. For 20β-ol; $^1$H NMR (CDCl$_3$, 250 MHz) δ 0.88 (t, 3, J=7.0 Hz, 16-CH$_2$CH$_3$), 0.97 (s, 3, 18-CH$_3$), 1.15 (d, 3, J=6.5 Hz, 6α-CH$_3$), 1.22 (d, 3, J=6.2 Hz, 21-H), 3.8 (m, 1, 20-H), 5.8 (s, 1, 4-H): IR (CHCl$_3$) 3400 (—OH), 1660 (conjugated 3-C=O), cm$^{-1}$; Anal. Calcd. for C$_{23}$H$_{34}$O$_2$: C, 80.65; H. 10.00. Found: C, 79.36; H, 9.95. For 20β-ol: $^1$H NMR (CDCl$_3$, 250 MHz), δ 0.86 (s, 3, 18-CH$_3$), 0.91 (t, 3, J=7.2 Hz, 16-CH$_2$CH$_3$), 1.15 (d, 3, J=6.5 Hz, 6α-CH$_3$), 1.26 (d, 3, J=6.2 Hz, 21-H), 3.8 (m, 1, 20-H), 5.8 (s, 1, 4-H).

Oxidation of the above 20-ol (230 mg) with oxalyl chloride and dimethylsulfoxide by the procedure in Example 1 afforded 165 mg of 6α-methyl-16α-ethyl-19-norpregna-4,9-diene-3,20-dione: mp=118°-119° C.; $^1$H NMR (CDCl$_3$, 250 MHz), δ 0.80 (s, 3, 18-CH$_3$), 0.82 (t, 3, J=7.1 Hz, 16-CH$_2$CH$_3$), 1.15 (d, 3, 6.5 Hz, 6α-CH$_3$), 2.15 (s, 3, 21-H), 5.8 (s, 1, 4-H): IR (CHC$_{13}$), 1705 (20-C=O), 1665 (conjugated 3-C=O) cm$^{-1}$; Anal. calcd. for C$_{23}$H$_{32}$O$_2$: C, 81.13; H, 9.47. Found: C, 81.01; H, 9.48.

This latter compound (410 mg, 1.2 mmol) was converted with ethylene glycol and p-toluenesulfonic acid by the procedure of Example 1 to 3,3,20,20-bis- (ethylenedioxy)-6α-methyl-16α-ethyl-19-norpregna-5(10),9(11)-diene (320 mg): $^1$H NMR (CDCl$_3$, 90 MHz) δ 0.80 (s, 3, 18-CH$_3$), 0.85 (t, 3, J=7 Hz, 16-CH$_2$CH$_3$), 1.1 (d, 3, J=6.5 Hz, 6α-CH$_3$), 2.1 (s, 3, 21-H), 3.8-4.0 (m, 8, 3,20-ketals), 5.5 (bs, 1, 11-H).

Epoxidation of the bisketal (305 mg. 0.71 mmol) with m-chloroperbenzoic acid (220 mg, 1.28 mmol) followed by the copper catalyzed Grignard addition procedure of Example 1 gave 1.2 g of dark blue residue containing 3,3,20,20-(ethylenedioxy)-6α-methyl-16α-ethyl-11β-(4-N,N-dimethylaminophenyl)-19-nor-9-pregnen-5α-ol.

Without further purification, the above material was treated with 70% aqueous acetic acid and then heated at 50° C. for 40 min. The reaction mixture was poured into ice water and neutralized with 10% (w/v) NaHCO$_3$ solution. The product was extracted with CH$_2$Cl$_2$, dried over sodium sulfate (anhydrous), filtered and concentrated to give 240 mg of dark blue solid. Column chromatography (SiO$_2$; 5% acetone-CH$_2$Cl$_2$) provided 42 mg of a single spot (TLC) material. An HPLC analysis (Zorbax-ODS 4.6 mm×25 cm. 15% H$_2$O in MeOH) showed that the product consisted of 6α and 6β-methyl isomers in an approximate ratio of 2:1. A preparative Rp-C18 column chromatography (20% H$_2$O in MeOH) provided 7.0 mg of 6α-methyl-16α-ethyl-11β-(4-N,N-dimethylaminophenyl)-19-norpregna-4,9-diene-3,20-dione and 2.5 mg of 6β-methyl-16α-ethyl-11β-(4-N,N-dimethylaminophenyl)-19-norpregna-4,9-diene-3,20-dione, together with 15 mg of unresolved mixture. For 6α-methyl compound: mp=95°-98° C.; $^1$H NMR (CDCl$_3$, 250 MHz) δ 0.36 (s, 3, 18-CH$_3$), 0.82 (t, 3, J=7.2 Hz, 16-CH$_2$CH$_3$), 1.22 (d, 3, J=6.5 Hz, 6α-CH$_3$), 2.16 (s, 3, 21-H), 2.9 (s, 6, N(CH$_3$)$_2$), 4.32 (d, 1, J=6.7 Hz, 11α-H), 5.88 (s, 1, 4-H), 6.6 (d, 2, J=8.7 Hz, aromatic-H ortho to N(CH$_3$)$_2$), 6.98 (d, 2, J=8.7 Hz, aromatic-H meta to N(CH$_3$)$_2$) IR (CHC$_{13}$) 1702 (20-C=O), 1660 (conjugated 3-C=O) cm$^1$; UV (MeOH) λ$_{max}$301, 260 nm; MS calcd. 459.3137. Found: 459.3141; Anal. calcd. for C$_{31}$H$_{41}$NO$_2$; C, 80.99; H, 8.92; N, 3.04. Found: C, 80.18; H, 9.02; N, 2.94. For the 6β-methyl isomer: $^1$H NMR (CDCl$_3$, 250 MHz) δ 0.39 (s, 3, 18-CH$_3$), 0.82 (t, 3, J=7.2 Hz, 16-CH$_2$CH$_3$), 1.28 (d, 3, J=7.1 Hz, 6α-CH$_3$), 2.17 (s, 3, 21-H), 2.9 (s, 6, N(CH$_3$)$_2$), 4.33 (d, 1, J=6.7 Hz, 11α-H), 5.78 (s, 1, 4-H), 6.6 (d, 2, J=8.7 Hz, aromatic-H ortho to N(CH$_3$)$_2$), 6.98 (d, 2, J=8.7 Hz, aromatic-H meta to —N(CH$_3$)$_2$).

EXAMPLE 4

Synthesis of 16α-Ethyl-11β-(4-N,N-dimethylaminophenyl)-19-norpregna-4,9-diene-3,20-dione A solution of sodium hydride (0.27 g, 11.3 mmol) in anhydrous dimethyl sulfoxide (15 mL) was heated at 75° C. for 1 hour. The reaction mixture was then cooled to room temperature and a solution of ethyl triphenylphosphonium iodide (4.6 g, 11.3 mmol) in dimethyl sulfoxide (10 mL) was slowly added. After stirring at room temperature for 15 min, a solution of 3,3-ethylenedioxy-11β-(4-N,N-dimethylaminophenyl-5α-hydroxyestr-9-en-17-one (prepared according to Cook et al., U.S. patent application Ser. No. 908,288 (1.0 g, 2.2 mmol) in anhydrous toluene (25 mL) was added dropwise, and the reaction mixture was subsequently heated at 80° C. for 2 hours. The solution was cautiously poured into ice water (250 mL) and extracted with methylene chloride (3×150 mL). The combined extracts were washed with water (2×50 mL) and brine. Removal of the dried (Na$_2$SO$_4$) solvent in vacuo yielded the crude product which was purified by elution from silica gel (50 g) using 1:1 ether-hexane containing 0.1% Et$_3$N to give 0.69 g (68%) of 3,3-ethylenedioxy-11β-(4-N,N-dimethylaminophenyl)-19-norpregna-9,17(20)-dien-5α-ol: mp=174°-177° C.; IR (CHCl$_3$) 3600 cm$^{-1}$; $^1$H NMR (250 MHz, CDCl$_3$) δ 0.56 (s, 3, 18-H), 2.91 (s, 6, NMe$_2$), 3.98 (m, 4, OCH$_2$CH$_2$O), 4.19 (m, s, 11-H), 4.29 (s, 1, 5-OH), 5.08 (m, 1, 20-H), 6.50 (d, J=9 Hz, 2, ArH ortho to NMe2), 7.09 (d, J=9 Hz, 2, ArH meta to NMe$_2$). Mass spectrum: m/z required for C$_{30}$H$_{41}$NO$_3$: 463.3086. Found: 463.3085. Anal. Calcd for C$_{30}$H$_{41}$NO$_3$: C, 77.71; H, 8.91; N, 3.02. Found: C, 77.45; H, 8.93; N, 2.95.

Oxygen gas was slowly bubbled through a solution of the above olefin (0.33 g. 0.7 mmol) and hematoporphyrin (15 mg) in pyridine (7 mL), while the solution was irradiated with a fluorescent lamp (25 w) placed 7 cm from the reaction flask. After 3 days, the bubbling of oxygen was discontinued. To this reaction mixture was then added acetic anhydride (3 mL), and the solution stirred at room temperature for 2 hours. The solvents were then removed in vacuo at room temperature, and the residue eluted from silica gel (50 g) using 2% acetone in methylene chloride containing 0.1% Et$_3$N to give 140 mg of unchanged starting material. Continued elution with 4% acetone in methylene chloride containing 0.1% Et$_3$N yielded 3,3-ethylenedioxy-11β-(4-N,N-dimethylaminophenyl)-5α-hydroxy-19-norpregna-9,16-dien-20-one (55 mg, 30% based on recovered starting material) as crystals; mp=225°-228° C.; IR (CHC$_{13}$) 3600, 1675 cm$^{-1}$; $^1$H NMR (250 MHz, CDCl$_3$) δ 0.59 (s, 3, 18-H), 2.24 (s, 3, 21-H), 2.90 (s, 6, NMe$_2$), 3.98 (m, 4, OCH$_2$CH$_2$O), 4.18 (m, 1, 11-H), 4.37 (s, 1, 5-OH), 6.65 (d, J=9 Hz, 2, ArH ortho to NMe2), 6.67 (apparent s, 1, 16-H), 7.10 (d, J=9 Hz, 1, ArH meta to NMe$_2$). Mass spectrum: m/z required for C$_{30}$H$_{39}$NO$_4$ (M$^+$-18); 459.2773. Found: 459.2774. Anal. Calcd for C$_{30}$H$_{39}$NO$_4$·½H$_2$O: C, 74.88; H, 8.24; N, 2.90. Found: C, 74.72; H, 8.31; N, 2.86.

To a cold (0° C.), stirred suspension of copper bromide-dimethyl sulfide complex (120 mg, 0.58 mmol) in anhydrous tetrahydrofuran (1 mL) was slowly added 0.4 mL (2.0 molar, 0.8 mmol) of ethylmagnesium bromide in tetrahydrofuran. After stirring at 0° for 0.5 h, the Grignard complex was rapidly added to a cold (0° C.), stirred solution of the above unsaturated ketone (16 mg, 0.034 mmol) in tetrahydrofuran (0.5 mL). After stirring at 0° C. for 2 h, the reaction mixture was added dropwise to a cold (0° C.), rapidly stirred solution of 3 N hydrochloric acid (1 mL). After stirring at room temperature for 2 h, the mixture was poured into a saturated solution of sodium bicarbonate (10 mL) and extracted with ethyl acetate (3×25 mL). The combined extracts were washed with water (2×50 mL) and brine. Removal of the dried (Na$_2$SO$_4$) solvent in vacuo yielded the crude product which was purified by elution from a reverse phase C-8 column (size B, E. M. Merck) using 85% aqueous methanol to yield 11 mg (80%) of 16α-ethyl-11β-(4-N,N-dimethylaminophenyl)-19-norpregna-4,9-diene-3,20-dione as off-white crystals; mp=168°-171° C.; IR (CHCl$_3$) 1720, 1680 cm$^{-1}$; $^1$H NMR (250 MHz, CDCl$_3$) δ 0.36 (s, 3, 18-H), 0.82 (t, 3, J=7 Hz, CH$_2$CH$_3$), 2.16 (s, 3, 21-H), 2.91 (s, 6, NMe$_2$), 4.32 (m, 1, 11-H), 5.76 (s, 1, 4-H), 6.64 (d, J=9 Hz, 2, ArH ortho to NMe2), 6.98 (d, J=9 Hz, 2, ArH meta to NMe$_2$). Mass spectrum: m/z required for C$_{30}$H$_{39}$NO$_2$; 445.2981. Found: 445.2977. Anal. Calcd for $C_{30}H_{39}NO_2$: C, 80.85 H, 8.82; N, 3.14. Found: C, 80.75; H, 8.85; N, 3.09.

EXAMPLE 5

Synthesis of 11β-(4-N,N-Dimethylaminophenyl)-19-norpregna-4,9,16-triene-3,20-dione To a cold (0° C.) stirred solution of hydrochloric acid (3 N, 1 mL) was slowly added a solution of 3,3-ethylenedioxy-11β-(4-N,N-dimethylaminophenyl)-5α-hydroxy-19-norpregna-5,16-dien-20-one (23 mg, 0.05 mmol) in tetrahydrofuran (2 mL). After being stirred at room temperature for 2 h, the reaction mixture was poured into a saturated solution of sodium bicarbonate (10 mL) and extracted with methylene chloride (3×20 mL). The combined extracts were washed with water (2×20 mL) and brine. Removal of the dried ($Na_2SO_4$) solvent in vacuo gave the crude product, which was purified by elution from silica gel (0.5 g using 1% acetone-methylene chloride containing 0.1% $Et_3N$) to yield 12 mg (50%) of 11β-(4-N,N-dimethylaminophenyl)-19-norpregna-4,9,16-triene-3,20-dione as a foam; IR ($CHCl_3$) 1675 cm$^{-1}$; $^1H$ NMR (250 MHz, $CDCl_3$) δ 0.66 (s, 3, 18-H), 2.26 (s, 3, 21-H), 2.91 (s, 6, $NMe_2$), 4.28 (m, 1, 11-H), 5.75 (s, 1, 4-H), 6.60 (d, J=9 Hz, 2, ArH ortho to $NMe_2$), 6.68 (apparent s, 1, 16-H), 7.06 (d, J=9 Hz, 2, ArH meta to $NMe_2$). Mass spectrum: m/z required for $C_{28}H_{33}NO_2$; 415.2511. Found: 415.2513.

EXAMPLE 6

Synthesis of 11β-(4-N,N-Dimethylaminophenyl)-19-norpregna-4,9-diene-3,20-dione 3,3-Ethylenedioxy-11β-(4-N,N-dimethylaminophenyl-5α-hydroxy-19-norpregna-9,16-diene-3,20-dione in ethanol solution was reduced with hydrogen in the presence of 5% palladium on charcoal. After one mole of hydrogen per mole of steroid was taken up, the solution was filtered and treated with hydrochloric acid in ethanol as described in Example 1. Evaporation left a residue which was purified by chromatography to yield 11β-(4-N,N-dimethylaminophenyl)-19-norpregna-4,9-diene-3,20-dione.

EXAMPLE 7

Synthesis of 11β-(4-N,N-Dimethylaminophenyl)-19-norpregna-4,9,17(20)-trien-3-one 3,3-Ethylenedioxy-11β-(4-N,N-dimethylaminophenyl)-19-norpregna-9,17(20)-dien-5α-ol was treated with hydrochloric acid in ethanol as described in Example 1 and purified by chromatography to yield 11β-(4-N,N-dimethylaminophenyl)-19-norpregna-4,9,17(20)-trien-3-one.

EXAMPLE 8

Synthesis of 11β-(4-acetylphenyl-19-norpregna-4,9,16-triene-3,20-dione

By the procedure described in Example 1 for the synthesis of 6α-methyl-11β-(4-N,N-dimethylaminophenyl)-3,3,20,20-bis(ethylenedioxy)-19-norpregn-9-ene-5α,17α-diol from 6α-methyl-3,3,20,20-bis(ethylenedioxy)-19-norpregna-5(10),9(11)-dien-17α-ol, but substituting 2-(4-bromomagnesiumphenyl)-2,5,5-trimethyl-1,3-dioxane for p-N,N-dimethylaminophenyl-magnesium bromide, 3,3-(ethylenedioxy)estra-5(10),9(11)-dien-17-one was converted to 3,3-ethylenedioxy-5α-hydroxy-11β-[4-(2,5,5-trimethyl-1,3-dioxan-2-yl)phenyl]estr-9-en-17-one. The latter compound was subjected to the procedures of Example 4 for converting 3,3-ethylenedioxy-11β-(4-N,N-dimethylaminophenyl)-5α-hydroxy-9-estren-17-one to 3,3-ethylenedioxy-11β-(4-N,N-dimethylaminophenyl)-5α-hydroxy-19-norpregna-9,16-dien-20-one followed by acid hydrolysis as described in Example 5 to yield 11β-(4-acetylphenyl)-19-norpregna-4,9,16-triene-3,20-dione, m.p. around 194°-197° C. Mass spectrum: m/z required for $C_{28}H_{30}O_3$: 414.2195. Found: 414.2189.

EXAMPLE 9

In Vitro Binding to Receptors

The in vitro activity of the subject compounds was determined by measuring the binding affinities (RBA) of these compounds relative to progesterone for the progesterone receptor in the cytosol obtained from estrogen-primed immature rabbit uterus and by measuring the RBA relative to dexamethasone for the glucocorticoid receptor from thymus of adrenalectomized rats. These assays were carried out by the procedures of J.R. Reel et al., *Fertility and Sterility*, 31, 552 (1979) (progesterone) and G. P. Chrousos et al., *Endocrinology*, 107, 472 (1980) (glucocorticoid). The results are presented in Table 1.

TABLE I

RELATIVE RECEPTOR BINDING ACTIVITY

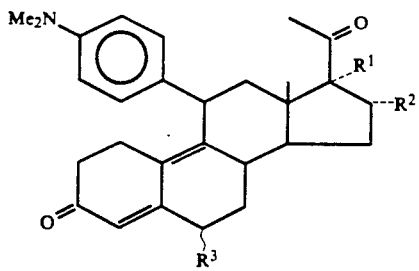

| Compound | | | Progestin | Glucocort. | |
|---|---|---|---|---|---|
| $R_1$ | $R_2$ | $R_3$ | RBA[a] | RBA[b] | P-RBA/G-RBA[c] |
| —OAc | —H | —H | 47 | 198 | 0.24 |
| —OAc | —H | α-$CH_3$ | 43 | 242 | 0.18 |
| —OAc | —H | β-$CH_3$ | 15 | ND | — |
| —OH | —H | —H | 15 | 41 | 0.37 |
| —OH | —H | α-$CH_3$ | 46 | 175 | 0.26 |
| —H | —Et | —H | 80 | 124 | 0.65 |
| —H | —Et | α-$CH_3$ | 61 | 246 | 0.42 |
| —H | —Et | β-$CH_3$ | 48 | 106 | 0.45 |
| $\Delta^{16}$ | | —H | 8 | ND | — |

[a]Relative ability to displace tritium-labeled progesterone from the receptor in uterine cytosol from estrogen-primed immature female rabbits as compared with progesterone (= 100).
[b]Relative ability to displace tritium-labeled dexamethasone from the receptor of the thymus of adrenalectomized rats as compared to dexamethasone (= 100).
[c]Ratio of RBA values for progesterone receptor (P-RBA) to glucocorticoid receptor (G-RBA).

EXAMPLE 10

In Vivo Antiprogestational Activity

The antiprogestational activity of the compounds was studied after both intrauterine and oral administration. In each case the compound was tested for its ability to inhibit the endometrial response due to subcutaneous administration of progesterone to estrogen-primed immature female rabbits. The methodology used for the intrauterine test has been described by D. A. McGinty et al. See Endocrinology, 24, 829 (1939). For oral administration of test compounds, the method used was analogous to that of Clauberg. See *Clauberg, Zentr. Gynakol.*, 54, 2757 (1930) as modified by McPhail *J. Physiol.* (London), 83, 145 (1935).

The results of the intrauterine tests are given in Table 2. Each active compound was characterized by a dose-related ability to block the progestational effect of simultaneously administered progesterone. When the percent inhibition was plotted versus the log of the dose, linear relationships were obtained. Linear regression analysis permitted calculation of the $ED_{50}$ and $ED_{90}$ values (the doses required for 50% and 90% inhibition of the progesterone effect, respectively). The actual dose which gave 90% or more inhibition is also given, although this value is probably less accurate than the calculated values which are based on the dose-response line. Very unexpectedly, these results do not correlate well at all with the in vitro binding studies. Since the intrauterine administration bypasses most of the drug-metabolizing systems of the body, especially the liver, intrinsic activity is expected to correlate reasonably well with binding activity to the receptor, according to currently held hypotheses regarding receptor binding. However although the 17α-acetoxy compounds bind well and also exhibit potent antiprogestational activity, the Δ-16 compound had even more potent activity even though its RBA was less than one-fifth of the value of the 17α-acetoxy compounds. Even more surprising was the lack of antiprogestational activity of the 16α-ethyl compounds, even though they exhibited the strongest binding to the progesterone receptor.

The 17α-acetoxy compounds also exhibited strong antiprogestational activity when given by the oral route, as is shown in Table 3 for 17α-acetoxy-6α-methyl-11β-(4-N,N-dimethylaminophenyl)-19-norpregna-4,9-diene-3,20-dione.

TABLE 2
SUMMARY OF ANTI-MCGINTY ACTIVITY

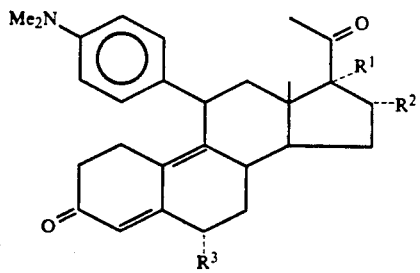

| Compound | $R_1$ | $R_2$ | $R_3$ | $ED_{50}$ (μg)[a] | $ED_{90}$ (μg)[a] | $ED_{90}$ (μg)[b] |
|---|---|---|---|---|---|---|
| 8a | —OAc | —H | —H | 0.41 | 1.2 | 2.0 |
| 8b | —OAc | —H | α-CH₃ | 0.54 | 1.9 | 2.0 |
| 19 | —H | —Et | —H | — | — | >>80[c] |
| 15a | —H | —Et | α-CH₃ | — | — | >>10[c] |
| 23 | Δ¹⁶ | | —H | 0.26 | 0.81 | 1.0 |
| RU-486 | | | | 0.28[d] | 0.87[d] | 1.0[d] |

[a] From % Inhib = a + b · ln dose
[b] Actual dose giving ≥90% inhibition
[c] No inhibition at tested dose
[d] Results variable. These data from "best run".

TABLE 3
Oral Antiprogestational Activity (Anti-Clauberg) of 17α-Acetoxy-6α-methyl-11β-(4-N,N-dimethylaminophenyl)-19-nor-pregna-4,9-diene-3.20-dione (15)

| N[a] | Total Oral Dose (mg) | Total SC Dose of Progesterone (mg) | Wt of Uterus (g ± SD) | McPhail Index (0–4) | % Inhibition[b] |
|---|---|---|---|---|---|
| 6 | 0.0 | 0.0 | 1.98 ± 0.40 | 0 | — |
| 6 | 0.0 | 0.8 | 3.06 ± 0.45 | 3.96 ± 0.04 | — |
| 6 | 1.0 | 0.8 | 3.26 ± 0.34 | 3.46 ± 0.12 | 12.7 ± 3.0 |
| 6 | 5.0 | 0.8 | 2.14 ± 0.22 | 1.92 ± 0.48 | 51.6 ± 12.2 |
| 5 | 10.0 | 0.8 | 2.24 ± 0.27 | 1.30 ± 0.24 | 67.2 ± 6.1 |

[a] Number of rabbits.
[b] Based on change in McPhail Index.

TABLE 4
PROGESTATIONAL ACTIVITY (MCGINTY ASSAY)

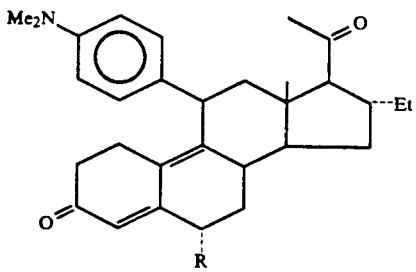

| R | Dose (μg) | McPhail Index Right Horn (Control) | McPhail Index Left Horn (Treated) |
|---|---|---|---|
| —H | 2.0 | 0 | 3.0 ± 0.32 |
| | 4.0 | 0 | 3.7 ± 0.12 |
| | 8.0 | 0 | 3.6 ± 0.10 |
| α-CH₃ | 20.0 | 0 | 3.8 ± 0.12 |
| | 40.0 | 0 | 3.9 ± 0.12 |
| | 80.0 | 0 | 3.8 ± 0.12 |

EXAMPLE 11

Progestational Activity in Vivo

The 16α-ethyl compounds which showed no antiprogestational activity were examined for progestational activity in the intrauterine assay. In this assay estrogen-primed immature female rabbits are treated by injection of the test compound into the left horn of the uterus while the right horn is left untreated as a control. Each horn is then scored for endometrial proliferation by the McPhail Index. As Table 4 shows, these compounds were potent progestational agents. This is a totally unexpected result, since all examples of prior art known to the inventors show that compounds which bind to the progesterone receptor and contain an 11β-(4-N,N-dimethylaminophenyl)-substituent exhibit antiprogestational activity. It indicates a possible need for reassessment of the current hypotheses regarding the effect of this substituent on antagonist versus agonist activity.

Obviously, numerous modifications and variations of the present invention are possible in light of the above teachings. It is therefore to be understood that within the scope of the present claims, the invention may be practiced otherwise than as specifically described herein.

What is claimed as new and desired to be secured by Letters Patent of the United States is:

1. An 11β-aryl-19-norprogesterone of the formula:

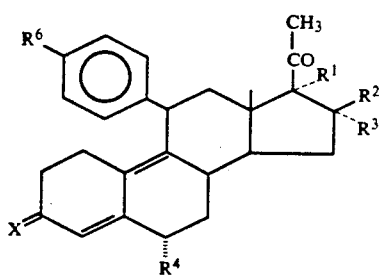

wherein:
(1) $R^1$ is $C_{2-4}$ alkenyl, $C_{2-4}$ alkynyl, $R^2$ is hydrogen, $R^3$ is H, $C_{1-4}$ alkyl, $C_{2-4}$ alkenyl, or $C_{2-4}$ alkynyl, $R^4$ is H, $CH_3$, F or Cl, $R^6$ is H, $(CH_3)_2N$, $CH_3O$, $CH_3CO$, $CH_3S$, $CH_3SO$ or $CH_3SO_2$ and X is O or $NOCH_3$; or (2) $R^1$ is H or $C_{1-4}$ alkyl, $R^2$ is hydrogen, $R^3$ is H, $C_{1-4}$ alkyl, $C_{2-4}$ alkenyl or $C_{2-4}$ alkynyl, $R^4$ is H, $CH_3$, F or Cl, $R^6$ is H, $CH_3CO$, $CH_3O$, $CH_3SO$ or $CH_3SO_2$ and X is O or $NOCH_3$; or (3) $R^1$ is H or $C_{1-4}$ alkyl, $R^2$ is hydrogen, $R^3$ is $C_{2-4}$ alkyl, $C_{2-4}$ alkenyl or $C_{2-4}$ alkynyl, $R^4$ is H, $CH_3$, F or Cl, $R^6$ is $CH_3O$, $CH_3CO$, H, $(CH_3)_2N$, $CH_3SO$ or $CH_3SO_2$ and X is O or $NOCH_3$.

2. The norprogesterone of claim 1, wherein $R^1$ is $C_{2-4}$ alkynyl.

3. The norprogesterone of claim 2, wherein $R^1$ is ethynyl.

4. The norprogesterone of claim 1, wherein $R^3$ is $C_{2-4}$ alkyl.

5. The norprogesterone of claim 4, wherein $R^3$ is ethyl.

6. The norprogesterone of claim 1, wherein $R^6$ is N,N-dimethylamino or acetyl.

7. The norprogesterone of claim 6, wherein $R^1$ is $C_{2-4}$ alkynyl.

8. The norprogesterone of claim 1, wherein $R^1$ and $R^3$ are hydrogen.

9. The norprogesterone of claim 8, wherein said norprogesterone is 11β-(4-acetylphenyl)-19-norpregna-4,9-diene-3,20-dione.

10. The norprogesterone of claim 2, wherein said norprogesterone is 17α-ethynyl-11β-(4,N,N-dimethylaminophenyl)-19-norpregna-4,9-diene-3,20-dione or 17α-ethynyl-11β-(4-acetylphenyl)-19-norpregna-4,9-diene-3,20-dione.

11. The norprogesterone of claim 5, wherein said norprogesterone is 16α-ethyl-11β-(4-N,N-dimethylaminophenyl)-19-norpregna-4,9-diene-3,20-dione or 16α-ethyl-6-α-methyl-11β-(4-N,N-dimethylaminophenyl)-19-norpregna-4,9-diene-3,20-dione.

12. The nonprogesterone of claim 1, wherein $R^1$ is H or $C_{1-4}$ alkyl, $R^2$ is hydrogen, $R^3$ is hydrogen, $C_{1-4}$ alkyl, $C_{2-4}$ alkenyl or $C_{2-4}$ alkynyl, $R^4$ is hydrogen, $CH_3$, F or Cl, $R^6$ is hydrogen, $CH_3CO$, $CH_3O$, $CH_3SO$ or $CH_3SO_2$ and X is O or $NOCH_3$.

13. The nonprogesterone of claim 1, wherein $R^1$ is hydrogen or $C_{1-4}$ alkyl, $R^2$ is hydrogen, $R^3$ is $C_{2-4}$ alkyl, $C_{2-4}$ alkenyl or $C_{2-4}$ alkynyl, $R^4$ is hydrogen, $CH_3$, F or Cl, $R^6$ is H $(CH_3)_2N$, $CH_3O$, $CH_3CO$, $CH_3SO$ or $CH_3SO_2$ and X is O or $NOCH_3$.

14. The nonprogesterone of claim 1, wherein $R^1$ is $C_{2-4}$ alkenyl or $C_{2-4}$ alkynyl, $R^2$ is hydrogen, $R^3$ is hydrogen, $C_{1-4}$ alkyl, $C_{2-4}$ alkenyl or $C_{2-4}$ alkynyl, $R^4$ is hydrogen, $CH_3$, F or Cl, $R^6$ is hydrogen, $(CH_3)_2N$, $CH_3O$, $CH_3CO$, $CH_3S$, $CH_3SO$ or $CH_3SO_2$ and X is O or $NOCH_3$.

15. The norprogesterone of claim 14, wherein $R^6$ is hydrogen, $CH_3O$, $CH_3CO$, $CH_3S$, $CH_3SO$ or $CH_3SO_2$.

16. The norprogesterone of claim 13, wherein $R^6$ is H, $CH_3O$, $CH_3CO$, $CH_3SO$ or $CH_3SO_2$.

* * * * *

UNITED STATES PATENT AND TRADEMARK OFFICE
CERTIFICATE OF CORRECTION

PATENT NO. : 5,073,548

DATED : DECEMBER 17, 1991

INVENTOR(S) : C. EDGAR COOK ET AL

Page 1 of 3

It is certified that error appears in the above-indentified patent and that said Letters Patent is hereby corrected as shown below:

On the title page, item [54] and column 1, line 2, "11 $\beta$-SUBSTITUTED" should read --11$\beta$-SUBSTITUTED--.

Column 1, line 46, "mefipristone" should read --mifepristone--;
line 50, "mefipristone" should read --mifepristone--;
line 55, "mefipristone" should read --mifepristone--;
line 61, "mefipristone" should read --mifepristone--;
line 65, "mefipristone" should read --mifepristone--.

Column 2, line 1, "mefipristone" should read --mifepristone--;
line 2, "mefipristone" should read --mifepristone--.

Column 8, line 59, "$C_{21}H_{30}O_3$:330,2095" should read --$C_{21}H_{30}O_3$:330.2095.

Column 9, line 25, "additional" should read --addition--;
line 56, "6$\alpha$-CH$_{3, 1.18}$" should read --6$\alpha$-CH$_3$, 1.18--.

Column 10, line 25, "CH$_2$C$_{12}$" should read --CH$_2$C$\ell_2$--;
line 30, "(CHC$_{13}$)" should read --(CHC$\ell_3$)--;
line 47, "68-methyl" should read --6$\beta$-methyl--.

Column 11, line 18, "19-norpregn-9-en-5$\alpha$-ol" should read --19-norpregn-9-en-5$\alpha$,17$\alpha$-diol--;
line 58, "68-methyl" should read --6$\beta$-methyl--.

UNITED STATES PATENT AND TRADEMARK OFFICE
CERTIFICATE OF CORRECTION

PATENT NO. : 5,073,548
DATED : DECEMBER 17, 1991
INVENTOR(S) : C. EDGAR COOK ET AL

Page 2 of 3

It is certified that error appears in the above-indentified patent and that said Letters Patent is hereby corrected as shown below:

Column 12, line 8, "tetrene" should read --tetraene--;
    line 15, "a" should read --an--;
    line 21, "17α,20β-diol" should read
        --17α,20α-diol--;
    line 29, "17α,20β-diol" should read
        --17α,20α-diol--;
    line 46, "m9" should read --mg--;
    line 54, delete "(25)".

Column 13, line 23, "6.8°-7.2" should read --6.8-7.2--;

Column 14, line 44, "20β-isomer" should read --20α-isomer--;
    line 52, "20β-ol" should read --20α-ol--.

Column 16, line 9, "NMe2" should read --NMe$_2$--.

Column 17, line 11, "5,16-dien-20-one" should read
    --9,16-dien-20-one--

Column 22, line 16, after "alkynyl", insert --or R$^3$ is C$_{2-4}$
    alkyl.--;
    line 30, "16α-ethyl-6-α" should read
    --16α-ethyl-6α--;

UNITED STATES PATENT AND TRADEMARK OFFICE
CERTIFICATE OF CORRECTION

PATENT NO. : 5,073,548
DATED : DECEMBER 17, 1991
INVENTOR(S) : C. EDGAR COOK ET AL

It is certified that error appears in the above-indentified patent and that said Letters Patent is hereby corrected as shown below:

Column 22, line 32, "nonproesterone" should read --norproesterone--;
    line 37, "nonproesterone" should read --norproesterone--;
    line 42, "nonproesterone" should read --norproesterone--;
    line 40, "H (CH$_3$)$_2$N" should read --H, (CH$_3$)$_2$N--.

Signed and Sealed this

Thirteenth Day of September, 1994

Attest:

BRUCE LEHMAN

Attesting Officer

Commissioner of Patents and Trademarks